United States Patent
Karapantsios et al.

(10) Patent No.: US 12,318,171 B2
(45) Date of Patent: Jun. 3, 2025

(54) SYSTEM AND METHOD FOR DETERMINING THE VASCULAR ENDOTHELIUM FUNCTIONALITY OF AN ARTERY

(71) Applicant: ARISTOTLE UNIVERSITY OF THESSALONIKI-ELKE, Salonika (GR)

(72) Inventors: Theodoros Karapantsios, Oreokastro (GR); Konstantinos Zacharias, Salonika (GR); Sotiris Evgenidis, Chortiatis (GR)

(73) Assignee: ARISTOTLE UNIVERSITY OF THESSALONIKI-ELKE, Salonika (GR)

( * ) Notice: Subject to any disclaimer, the term of this patent is extended or adjusted under 35 U.S.C. 154(b) by 0 days.

(21) Appl. No.: 18/696,528

(22) PCT Filed: Sep. 26, 2022

(86) PCT No.: PCT/EP2022/076698
§ 371 (c)(1),
(2) Date: Mar. 28, 2024

(87) PCT Pub. No.: WO2023/052300
PCT Pub. Date: Apr. 6, 2023

(65) Prior Publication Data
US 2024/0335122 A1    Oct. 10, 2024

(30) Foreign Application Priority Data
Sep. 29, 2021   (EP) .................................. 21386060

(51) Int. Cl.
*A61B 5/02*   (2006.01)
*A61B 5/00*   (2006.01)
(Continued)

(52) U.S. Cl.
CPC ........ *A61B 5/02007* (2013.01); *A61B 5/0053* (2013.01); *A61B 5/053* (2013.01);
(Continued)

(58) Field of Classification Search
None
See application file for complete search history.

(56) References Cited

U.S. PATENT DOCUMENTS

| | | |
|---|---|---|
| 2005/0070805 A1 | 3/2005 | Dafni |
| 2009/0281449 A1* | 11/2009 | Thrower .............. A61B 5/0031 600/547 |
| 2013/0331678 A1 | 12/2013 | Lading |

FOREIGN PATENT DOCUMENTS

| | | |
|---|---|---|
| EP | 3005942 A1 | 4/2016 |
| EP | 3245947 A1 | 11/2017 |

(Continued)

OTHER PUBLICATIONS

Chebyshev Filters, The Scientist and Engineer's Guide to Digital Signal Processing, https://www.analog.com/en/resources/technical-books/scientist_engineers_guide.html (Year: 1999).*

(Continued)

*Primary Examiner* — Daniel L Cerioni
*Assistant Examiner* — Om Patel
(74) *Attorney, Agent, or Firm* — George Likourezos; Carter, DeLuca & Farrell LLP

(57) ABSTRACT

A method for determining a vascular endothelium functionality of an artery of a person, the method comprising: acquiring measurement data associated with a series of electrical measurements taken by an electrical impedance spectroscopy device; extracting an impedance time series associated with the impedance changes of the of the medium intervening between each pair of electrodes; filtering the impedance time series in the frequency domain to extract at (Continued)

least a low pass frequency, LPF, and a band limited frequency, BPF, component waveforms for each pair of electrodes; processing the LPF and BPF component waveforms obtained from each pair of electrodes to extract a set of biomarker parameter values, each biomarker parameter being indicative of a particular aspect of the endothelium functionality of the artery of the person; and determining an endothelium functionality index indicative of the vascular endothelium functionality of the artery of the person.

14 Claims, 14 Drawing Sheets

(51) Int. Cl.
    *A61B 5/053*     (2021.01)
    *G16H 50/30*     (2018.01)

(52) U.S. Cl.
    CPC .............. *A61B 5/725* (2013.01); *A61B 5/726* (2013.01); *A61B 5/742* (2013.01); *G16H 50/30* (2018.01)

(56) References Cited

FOREIGN PATENT DOCUMENTS

WO      WO-2010032252 A1 *    3/2010   ........... A61B 5/0245
WO      WO-2012032553 A1 *    3/2012   ......... A61B 5/02108

OTHER PUBLICATIONS

International Search Report and Written Opinion issued in International Application No. PCT/EP2022/076698, dated Jan. 30, 2023, pp. 1-10.

Evgenidis, S.P., "Impedance Spectroscopy device for early indication and diagnosis of Coronary disease (Cor-•-Is)" XP055357914 (Mar. 2015) pp. 1-3.

Extended European Search Report issued by the European Patent Office in corresponding EP Patent Application No. 21386060.4, dated Mar. 1, 2022.

Communication under Rule 71(3) EPC, together with Text Intended for Grant (Clean copy), issued by the European Patent Office in corresponding EP Patent Application No. 21386060.4, dated Feb. 29, 2024.

* cited by examiner

*$\Delta Imp_{initial}$: LPF signal increase due to applied ischemia

*$\alpha_{initial}$: LPF signal increase gradient

*$\alpha_{initial}$: LPF signal increase gradient
$\alpha_{final}$: LPF signal decrease gradient

*Mag_initial: Amplitude of BPF signal Continuous Wavelet Transform prior to ischemia
Mag_final: Amplitude of BPF signal Continuous Wavelet Transform during hyperemia

SYSTEM AND METHOD FOR DETERMINING THE VASCULAR ENDOTHELIUM FUNCTIONALITY OF AN ARTERY

CROSS REFERENCE TO RELATED APPLICATIONS

The present application is a national stage application of International Application No. PCT/EP2022/076698, filed Sep. 26, 2022, which claims priority to European Patent Application No. 21386060.4, filed Sep. 29, 2021, the entire contents of which are incorporated herein by reference in their entirety.

FIELD

The present invention relates to a system and a method for determining the vascular endothelium functionality of an artery of a person.

BACKGROUND

It has been clinically confirmed that when cardiovascular risk factors exist (diabetes, hypertension, dyslipidemia, smoking, obesity and severe family history) the normal endothelial function is disrupted and the vasoconstrictive, prothrombotic and inflammatory activity of endothelium prevails. This condition is called endothelial dysfunction and assists in mobilizing and maintaining the mechanisms of atherogenesis, thus increasing the long-term risk of future cardiovascular events (e.g. coronary artery disease). The endothelial dysfunction is not limited to the coronary arteries, but covers the whole vascular system and further has been found that there's a strong correlation between endothelial function of coronary arteries with peripheral arteries (e.g. brachial, radial artery). This created the need for determining the endothelial functionality of peripheral arteries.

Methods for estimating and quantifying endothelial function are based on measurement of the endothelium-dependent vasodilation induced by the release of nitric oxide (NO) produced in the endothelial cells. When the nitric oxide is diffused into the smooth muscle cells of the artery it increases the concentration of cGMP (cyclic guanosine monophosphate) which leads to a decrease in the intracellular concentration of $Ca^{+2}$ ions and vasodilation. These methods comprise invasive or non-invasive techniques.

Invasive techniques, such as when performing a coronary angiography, were initially used to measure endothelial-dependent vasodilation in the coronary network before and after infusion of substances (acetylcholine) that cause the release of NO from the endothelium of the coronary vessels. Invasive techniques have also been applied to the peripheral arterial network by controlling the brachial artery via injection of endothelioactive substances into the brachial artery.

Non-invasive techniques, such as Flow Mediated Dilation (FMD), determine brachial artery dilation using ultrasounds following a transient period of ischemia. However, existing techniques based on ultrasound analysis have certain disadvantages. In particular, these techniques: 1) require an ultrasound device with high cost and specialized personnel for measurements, 2) have a low image resolution relative to the size of the vessel, 3) have limited repeatability and 4) shows insufficient imaging in obese persons.

Following the same medical principle, the endothelial functionality of brachial artery can be also assessed by means of electrical signals, in an effort to achieve non-invasive diagnosis of coronary artery disease. A non-invasive electrical impedance spectroscopy method is disclosed in EP3245947 and is based on the use of a device comprising a set of two non-invasive electrodes, i.e. a single pair of electrodes, that are configured to be attached on the skin of the person over and along a peripheral artery for obtaining a series of electrical measurements of the artery portion between the two electrodes, which are subsequently digitally processed by a personal computer to determine the endothelium functionality by comparing the electrical measurements taken before and after an ischemic cuff pressure is applied on the skin portion of the person.

Further enhancing the accuracy and sensitivity of the known non-invasive technique would enable the detection of changes in the endothelium functionality with greater sensitivity and accuracy, which would facilitate early detection of a cardiovascular disease such as coronary disease.

Therefore, there is a need to provide an improved non-invasive solution to enable and facilitate early as well as advanced and more accurate detection of endothelial dysfunction signs that would increase the risk of a person to a particular disease such as coronary disease.

SUMMARY OF THE INVENTION

An aim of the present invention is to provide an improved system and method for assessing of the vascular endothelium functionality of an artery of a person, with greater sensitivity and accuracy. As a result, the improved system and method enable early, convenient and reliable detection of changes and disruptions in the endothelial function which may be indicative of early signs of a cardiovascular disease.

The aim of the present invention is achieved according to the invention with the system and method showing the technical characteristics of the respective independent claims. Preferred embodiments of the present invention are disclosed in the dependent claims.

According to an aspect of the present invention, there is provided a computer implemented method for determining a vascular endothelium functionality of an artery of a person, the method comprising the steps of:
  acquiring measurement data associated with a series of electrical measurements obtained by an electrical impedance spectroscopy device using at least one pair of electrodes attached to a skin portion of a limb of the person along a portion of an artery under assessment, the electrical measurements being obtained over a period of time at different frequencies while the impedance spectroscopy device operates an ischemic cuff positioned on the limb of the person between a normal state, where no pressure is applied on the limb of the person, an ischemic state, where a desired pressure is applied on the limb of the person to restrict the flow of blood in the artery under assessment, and a hyperaemic state, where the pressure applied during the ischemic state is released;
  extracting, from the measurement data, an electrical impedance time series associated with the impedance changes of a medium intervening between each pair of electrodes, the medium comprising the portion of the artery, surrounding tissue, the skin portion, and blood flowing in the artery during the normal state, ischemic state, and hyperaemic state;
  filtering the electrical impedance time series in the frequency domain to extract at least a low pass frequency, LPF, component waveform and a band limited frequency, BPF, component waveform for each pair of electrodes; and determining the vascular endothelium functionality of the artery of the person by performing the steps of:

processing the LPF and BPF component waveforms obtained from each pair of electrodes to extract a set of biomarker parameter values, each biomarker parameter being indicative of a particular aspect of the endothelium functionality of the artery of the person; and determining, based on the biomarker parameter values, an endothelium functionality index indicative of the vascular endothelium functionality of the artery of the person.

The method of the present invention provides a spectral separation of the LPF and BFP components of the electrical impedance time series associated to the electrical measurements obtained by each of the pair of the electrodes. By filtering the electrical impedance time series in the frequency domain, certain characteristics of the LPF and BPF component waveforms are highlighted. The LPF and BPF component waveforms provide critical information for the assessment of endothelium functionality, an advantage which pre-existing techniques lacks. The method benefits of component waveforms obtained from each pair of electrodes to extract a set of biomarker parameter values associated with different aspects of the endothelium functionality and accordingly, based on the biometric parameters values determine an overall endothelium functionality index indicative of the vascular endothelium functionality of the artery of the person. As a result, the method provides, by means of the calculation of the biometric parameter values, a measurable indicator that more accurately reflects the internal state of the artery under assessment. Therefore, the present invention enables the accurate assessment of the endothelium functionality by extracting key information from the electrical measurements obtained from the electrode pairs. The information extracted from the LPF and BPF component waveforms are used to determine a set of biometric parameters associated with associated endothelium functionality during the operation of the ischemic cuff between the normal, ischemic, and hyperaemic states. In this way, it is possible to observe the endothelium functionality under different conditions and accordingly determine any changes that could attributed to a cardiovascular disease. Therefore, the present invention provides an improved, more convenient and accurate assessment of the endothelium functionality when compared to known non-invasive solutions.

Furthermore, the method presented herein, can measure with high sensitivity changes in electrical impedance caused by ischemic binding and reactive hyperaemia, but also signal fluctuations due to pulsed blood flow of the artery. As a result, the information obtained from the present invention can be used to provide an improved clinical evaluation of the endothelium functionality.

According to an embodiment of the present invention, the step of determining the vascular endothelium functionality further comprises the step of comparing the endothelium functionality index with a reference index.

According to an embodiment of the present invention, extracting the set of biomarker parameter values comprises the step of:

detecting from the measurement data the electrical impedance time series corresponding to each electrode pair used by the impedance spectroscopy device to take the electrical measurements; and wherein if more than one pair of electrodes is detected performing the step of:

determining the value of each biometric parameter in the set by averaging the corresponding biometric parameter values obtained from the LPF and BPF component waveforms extracted from each detected pair of electrodes.

Accordingly, the present method is configured to facilitate the determination of the endothelium functionality based on electrical measurement data obtained from a plurality of pair of electrodes e.g. four, six and the like. For example, the electrical impedance spectroscopy device may be provided with two pair of electrodes positioned on the skin portion of the person, to facilitate an improved detection of changes in the endothelium functionality. Accordingly, the present solution would extract and average the biometric parameter values extracted from the pair of electrodes to obtain a master set of biometric parameter values, which are used to determine the endothelium index. As a result, a more accurate assessment of the endothelium functionality is performed, which can facilitate the early diagnosis of cardiovascular diseases.

According to an embodiment of the present invention, the extraction of the impedance time series from the electrical measurements obtained from each pair of electrodes is obtained by:

filtering the measurement data using a digital zero-phase filter to obtain filtered data comprising an Infinite Impulse Response, IIR, Butterworth filter.

According to an embodiment of the present invention, step of extracting the impedance time series further comprises:

digitally processing the filtered data to obtain recovered data by performing the steps of:

generating an envelope signal of the filtered data by calculating absolute data of the filtered data;

digitally filtering the envelope signal using a digital low-pass filter with a standard cut-off frequency of 100 Hz to obtain the recovered data, wherein the digital low-pass filter is Chebyshev Type I IIR filter; and processing the recovered data to determine the impedance time series.

The use of an infinite Impulse Response, IIR, Butterworth filter, significantly reduces the Electromagnetic interferences (EMI) observed in the electrical measurement data obtained from the electrode pairs. As a result, by removing the EMI from the electrical measurement data, a more accurate detection of small fluctuations in the electrical measurement data may be detected e.g. in the order of ~0.01%. it has been found that the use of an IIR Butterworth reduces width fluctuations in the transit zone and further provides very high and effective rejection of EMI due to its very large attenuation characteristics e.g. of 180 dB at 6 kHz. In general, the IIR digital filters exhibit non-linear phase digital distortion. This results in a number of advantages such as: (a) the cancellation of phase distortion by the IIR filter which would otherwise lead to the appearance of a phase difference in the initial signal and (b) doubling the order of the Butterworth filter making the total rejection at 360 dB at 6 kHz, with the practical result that the interference outside the transit zone is completely discarded. As a result, the use of an IIR Butterworth filter ensures removal of EMI, thereby improving the quality of the electrical signals, which leads to the accurate detection of fluctuation in the impedance values of the medium intervening between the electrodes, i.e. the artery portion, surrounding tissues and muscles, the skin portion, and blood flow in the artery under different conditions e.g. normal state, ischemic state, hyperaemic state. A Chebyshev Type I IIR digital filter may be used to further improve the quality of the measurement data and remove unwanted noise.

According to further aspect of the present invention, there is provided a system for determining vascular endothelium functionality of an artery of a person comprising:

an ischemic cuff configured to be positioned on a limb of the person;

an electrical impedance spectroscopy configured to obtain a series of electrical measurements over a period of time at different frequencies associated with the endothelium functionality of an artery under assessment, the impedance spectroscopy device comprising at least one pair of electrodes configured to be attached to a skin portion of the limb of a person along a portion of the artery under assessment to obtain the series of electrical measurements of a medium intervening each pair of electrodes, the medium comprising the portion of the artery, surrounding tissue, the skin portion, and blood flowing in the artery during the normal state, ischemic state, and hyperaemic state, wherein the impedance spectroscopy device is configured to operate, during obtaining the series of electrical measurements from the at least one pair of electrodes, the ischemic cuff between a normal state, where no pressure is applied on the limb of the person, an ischemic state, where a pressure is applied on the limb of the person to restrict the flow of blood in the artery under assessment, and a hyperaemic state, where the pressure applied during the ischemic state is released;

a processing unit communicatively coupled to the impedance spectroscopy device and configured to perform the method of any one of claims 1 to 13; and a display configured to display the endothelium functionality index determined by the processing unit, which is indicative of the vascular endothelium functionality of the artery of the person and/or the results of a comparison between the determined endothelium functionality index and a reference endothelium functionality index.

According to an embodiment of the present invention, the electrical impedance spectroscopy device comprises a first pair of electrodes and a second pair of electrodes, wherein the second pair of electrodes is placed between the first pair of electrodes.

With the addition of second pair of electrodes with very high input resistance in the order of GΩ and in combination with the VCCS stimulation, parasitic currents are practically non-existent, and the measured voltages are more stable than those obtained with a single pair of electrodes. In addition, with this configuration the second pair of electrodes is not affected by the electrical resistance that exists between the electrode and the skin, because there is no stimulation current flow $I_{out}$ between the electrodes. It should be noted that further pair of electrodes could be added to further improve the electrical measurements.

According to further aspect of the present invention, there is provided a computer program loaded on a memory of a processing unit, which when executed causes the processing unit to assess the endothelium functionality according to embodiments of the present invention.

BRIEF DESCRIPTION OF THE DRAWINGS

Embodiments of the invention will now be described, by way of example, with reference to the accompanying drawings, in which.

DETAILED DESCRIPTION

The present invention will be illustrated using the exemplified embodiments shown in the figures, which will be described in more detail below. It should be noted that any references made to dimensions are only indicative and do not restrict the invention in any way. While this invention has been shown and described with reference to certain illustrated embodiments thereof, it will be understood by those skilled in the art that various changes in form and details may be made therein without departing from the scope of the invention.

Figure 1:
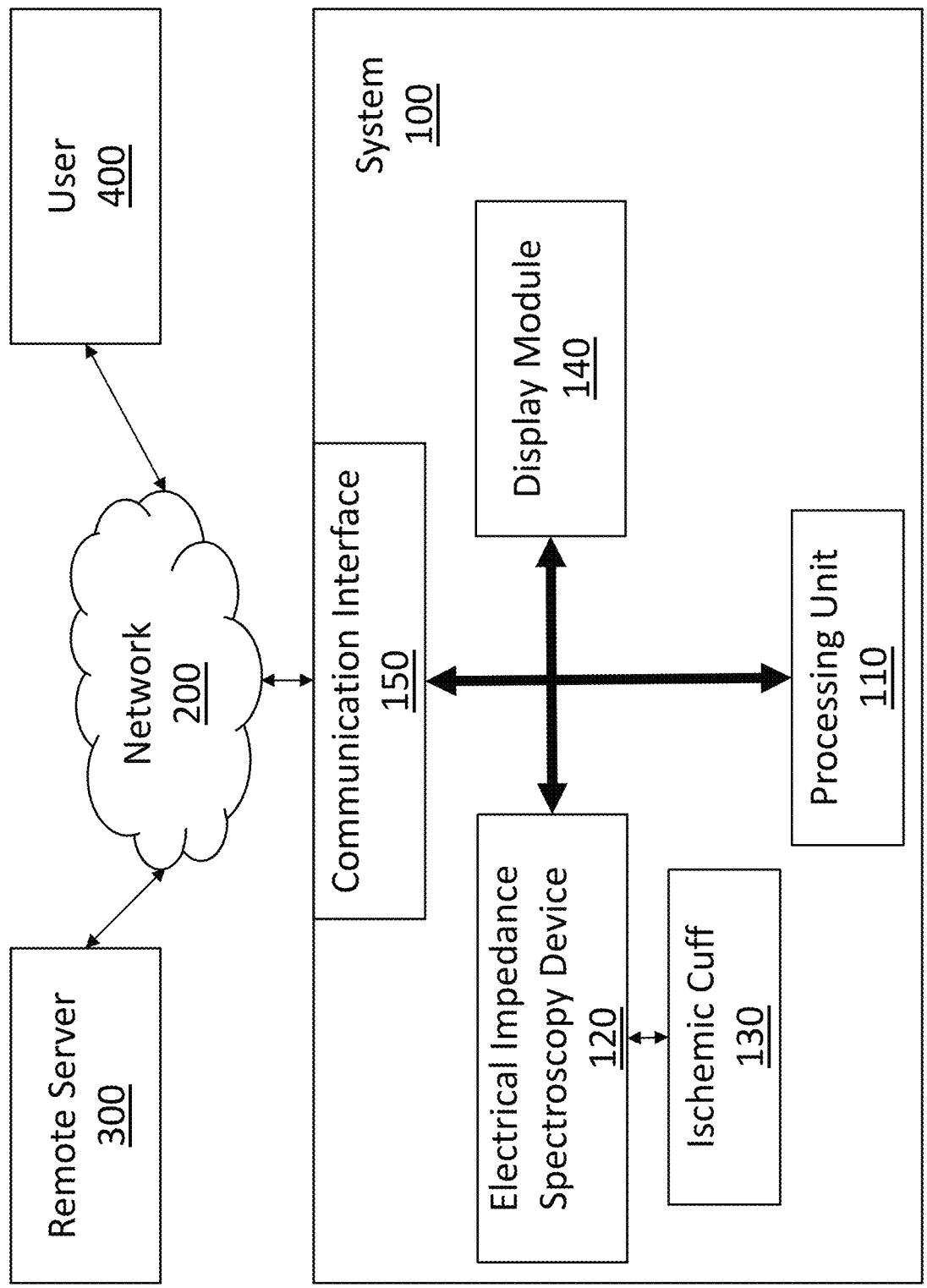
FIG. 1 illustrates a schematic diagram showing an exemplified system for determining the vascular endothelium functionality of an artery of a person according to embodiments of the present invention.

FIG. 1 is a schematic diagram showing an exemplified system 100 for assessing the vascular endothelium functionality of an artery of a person according to embodiments of the present invention. At a high level, the example system 100 includes an ischemic cuff 130, an electrical impedance spectroscopy device 120 and a display module 140 that are communicatively coupled to a processing unit 110.

The processing unit 110 may include one or more processing components, which may be referred to as "processors" or "central processing units" (CPUs), configured to execute instructions for the assessment of endothelium functionality. In some implementations, the processing unit 110 can be configured to output the result of the processing, such as a measurement report or an endothelium functionality index. The processing unit 110 can be configured to receive information, such as electrode measurements from the impedance spectroscopy device 120 and/or other information. The processing unit 110 can also include other auxiliary components, such as random-access memory (RAM) and read-only memory (ROM).

The example system 100 further comprises a communication interface 150 configured to interface with a network 200 for communicating the result of the processing performed by the processing unit 110 to a remote server 300 or a user device 400.

The electrical impedance spectroscopy device 120 comprises at least one pair of electrodes configured to be attached on the skin of a person along a portion of the artery to generate a series of electrical measurements of the medium intervening between these electrodes, which includes, but not limited, to the vessels surrounded by the human tissues and skin, and blood flowing in the artery under the different conditions. The electrical measurements can be impedance measurements $Z_m$ or voltage measurements $V_m$ using at least one pair of electrodes attached to the skin of a limb of the person along a portion of an artery under assessment. The electrical impedance spectroscopy device 120 operates an ischemic cuff 130 configured to be positioned on a limb of the person e.g. around the arm, to restrict the flow of blood in the artery under assessment. The electrical measurements are obtained by the impedance spectroscopy device 120 during the operation of the ischemic cuff between a normal state, where no pressure is applied on the limb of the person, an ischemic state, where a desired pressure is applied on the limb of the person to restrict the flow of blood in the artery under assessment, and a hyperaemic state, where the pressure applied during the ischemic state is released.

The impedance spectroscopy device 120 is not limited to the geometry of electrodes, which can be vary and include rings, flat surfaces or any other type of geometry.

FIGS. 2 to 6 provide exemplified implementation of an electrical impedance spectroscopy device 120 according to embodiments of the present invention.

Figures 2, 3:
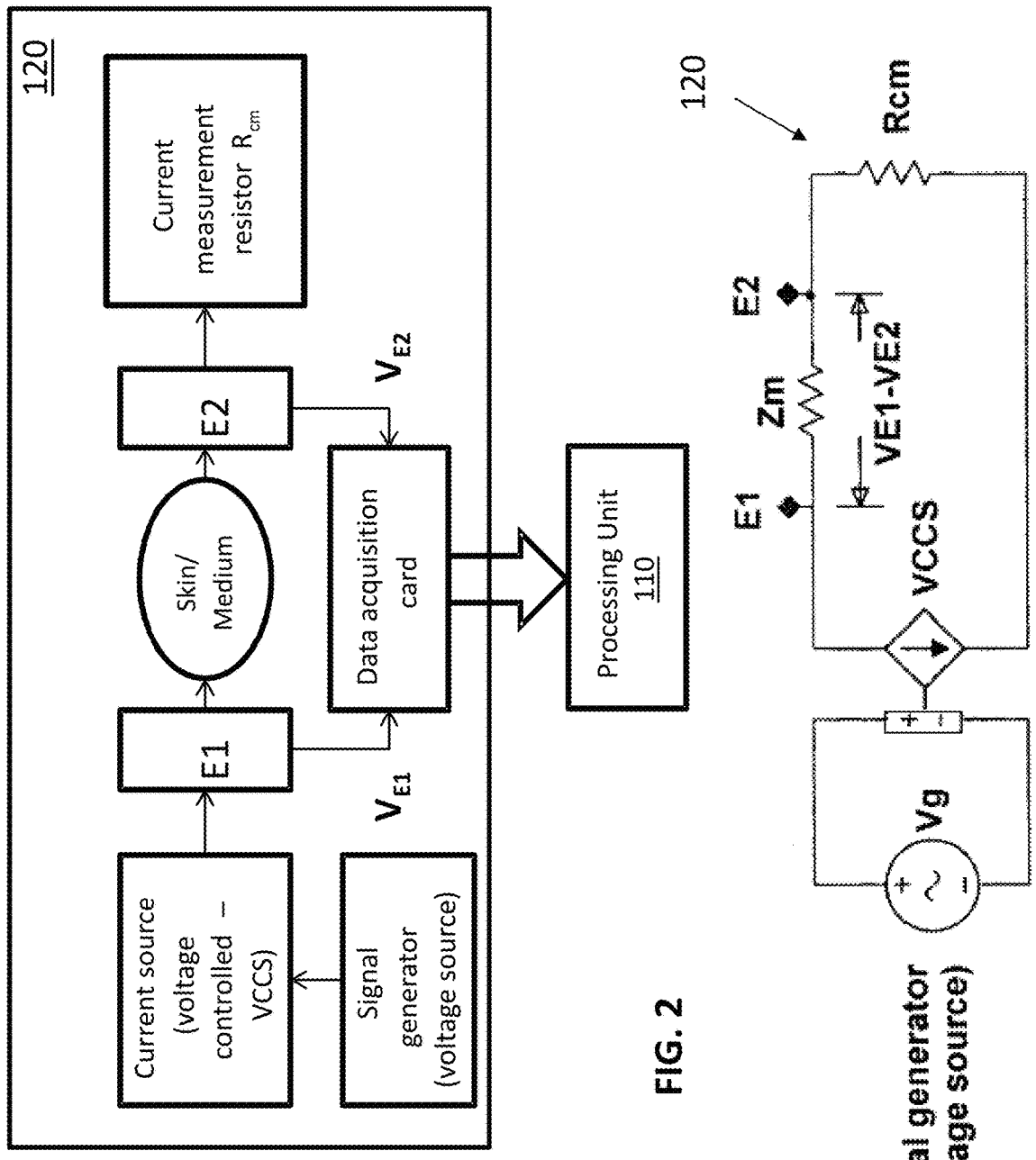
FIG. 2 illustrates a schematic diagram of an exemplified electrical impedance spectroscopy device comprising a single pair of electrodes E1 and E2 according to embodiments of the present invention.
FIG. 3 illustrates an electrical schematic of the electrical impedance spectroscopy device shown in FIG. 2 according to embodiments of the present invention.

Reference is now made to FIG. 2 where there is provided a schematic diagram of the device 120 comprising a single pair of electrodes E1 and E2. The electrical schematic of the impedance spectroscopy devices 120 is shown in FIG. 3. This device 120 additionally comprises a voltage controlled current source (VCCS) that is controlled by a signal generator (voltage source). The VCCS is a component that converts any type of voltage source, such as sinusoidal, square, triangular, or pulse waves etc., of any voltage amplitude and frequency, into a current source. The VCCS is placed between the signal generator and the electrode E1 to provide the required AC current signal of a desired width and frequency as determined after frequency scanning (spectroscopy technique).

As will be appreciated, the AC current signal provided by the VCCS causes a voltage drop between electrodes E1 and E2 when obtaining electrical measurement of the skin. The voltage drop can be obtained as:

$$V_m = V_{E1} - V_{E2} \quad (1)$$

The measured impedance measured by the electrodes E1 and E2, is the magnitude of $Z_m$ and can be simply calculated as the ratio of the differential voltage (voltage drop) between E1 and E2 and output current $I_{out}$:

$$Z_m = \frac{V_{E1} - V_{E2}}{I_{out}} = \frac{V_m}{I_{out}} \quad (2)$$

The device 120 further comprises an optional resistor $R_{cm}$ for the measurement of the output current $I_{out}$. The voltage difference $V_{CM}$ at the resistor $R_{cm}$ can be obtained as:

$$V_{CM} = R_{CM} I_{CM} = R_{CM} |I_{CM}| e^{j\phi_0} \quad (3)$$

Resolving the above equation per $I_{CM}$, the voltage drop $V_m$ between electrodes E1 and E2 can therefore be described as:

$$V_m = |Z_m||I_{CM}|e^{j\phi_m} \quad (4)$$

Wherein $Z_m$ is the equivalent impedance as measured by the two electrodes E1 and E2. The phase shift/difference $\Delta\phi$ of the waveform can obtained as the phase angle of the ratio between $V_m$ and $V_{CM}$. The phase difference $\Delta\phi$ can thus be obtained as follows:

$$\Delta\phi = \arg\left(\frac{V_m}{V_{cm}}\right) = \arg\left(\frac{|Z_m||I_{CM}|e^{j\phi_m}}{R_{CM}|I_{CM}|e^{j\phi_0}}\right) = \arg\left(\frac{|Z_m|}{R_{CM}}e^{j\phi_m - \phi_0}\right) = \phi_m - \phi_0 \quad (5)$$

In the condition where there's no phase shift, the impedance $Z_m$ is transformed to resistance $R_m$. The voltage difference $V_{E1}-V_{E2}$ is the measured key parameter ($I_{out}$ is constant), because it is directly affected by the impedance variation due to blood flow in the artery.

Figure 4:
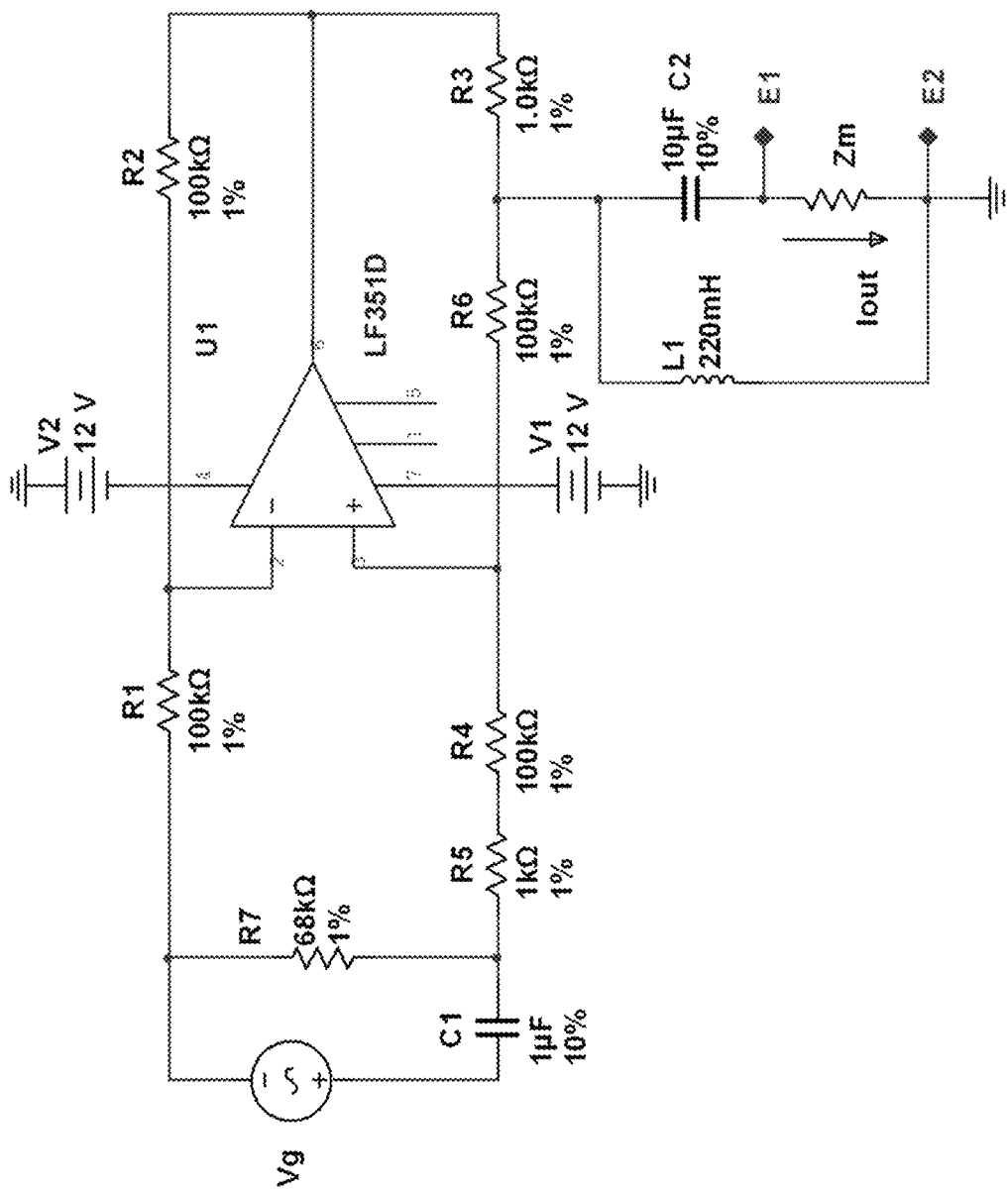
FIG. 4 illustrates an exemplified electrical schematic of the electrical impedance spectroscopy device using a modified and improved VCCS circuit for AC, according to an embodiment of the present invention.

The VCCS is a transconductance device and the most common use is as transconductance amplifier (TA) which design is shown in the electrical schematic of FIG. 4, according to an implementation. The transconductance amplifier is like a typical voltage amplifier but the amplified output is a current. It is an amplifier because the magnitude of the transfer function is $$|H_{TA}| = \frac{I_o}{V_i} > 1,$$

where $I_o$ is the output current and $V_i$ is the input voltage. For the application of the present invention on humans and because of safety reasons and regulations, the excitation current does not exceed 2 mA. Therefore, the majority of biomedical devices operate with a stimulation current having a typical value of 0.1 mA. As a result, the practical implementation of the VCCS would require the current output to be in mA range and the voltage input in V range. Hence the magnitude of the transfer function of VCCS $|H_{VCCS}|$ would be far less than one:

$$|H_{VCCS}| = \frac{I_{out}}{V_i} = \frac{mA}{V} \ll 1 \qquad (6)$$

As regards the application of present invention on humans, the magnitude of the transfer function or gain is set to be:

$$|H_{VCCS}| = \frac{1 \; mA}{1 \; V} = 0.001 \qquad (7)$$

With that gain, 1V of the voltage source is transformed (converted) into 1 mA current excitation passing through the electrode E1. In the case that it is considered necessary, the VCCS gain could be adjusted (increased or decreased) at any desired value. The VCCS is essentially a high impedance current source and many alternative designs of current sources and VCCS exist. Most of the designs are for current sources controlled by a DC voltage source. But for the demanding application of endothelium functionality detection of peripheral artery and consequently of the coronary artery network a versatile and reliable alternating current source (AC current) is needed, with high output impedance and wide frequency range. The gain in the VCCS circuit is set by $R_3$ and ratio of $R_1/R_2$ (which is typically 1/1). In this design, the ratio of $(R_5+R_4)/(R_6+R_3)$ should be matched with $R_1/R_2$ for proper biasing of the operational amplifier, so:

$$\frac{R_5 + R_4}{R_6 + R_3} = \frac{R_1}{R_2} \qquad (8)$$

The gain then is:

$$|H_{VCCS}| = \frac{I_{out}}{V_g} = \frac{1}{R_3} \qquad (9)$$

Consequently, low values for $R_3$ can be used and have all the other resistors high in value, such as 100 kΩ or 1 MΩ, as shown in FIG. 4. Based on Equations 8 and 9, the value of the resistor would be $R_3$=1 kΩ ($R_3$ value may be decreased, if increased detection sensitivity is required). Therefore, the output impedance of the current source is very high, and even for typical operational amplifier with CMRR of 60 dB, the output impedance would "degrade" to 10 MΩ (acceptable value in biomedical applications). The majority of commercial operational amplifiers have CMRR (Common Mode Rejection Ratio) higher than 80 dB, so the impedance is increased even more. This circuit can supply many milliamperes (or as low as microamperes) depending on the input voltage and VCCS gain. Also, with a power supply of at +12V DC (nominal voltage values), the maximum resulting voltages caused by the output current, can be as large as 10 V, with good efficiency. If higher resulting voltages are needed, the power supply voltage can be increased.

The operation amplifier is the integrated circuit LF351D, which is a JFET operational amplifier, with internal frequency compensation, high CMRR 100 dB, high slew rate 13V/μs, low noise and distortion 0,003% (typical). Test measurements have shown that even for the case of a high value 1 kΩ load, the gain is dropped only about 0.4% and a phase shift of −5.7° is observed. But these deviations are negligible and do not affect the accuracy of the measurements because when applying the technique, a baseline measurement is always taken.

Figure 5:
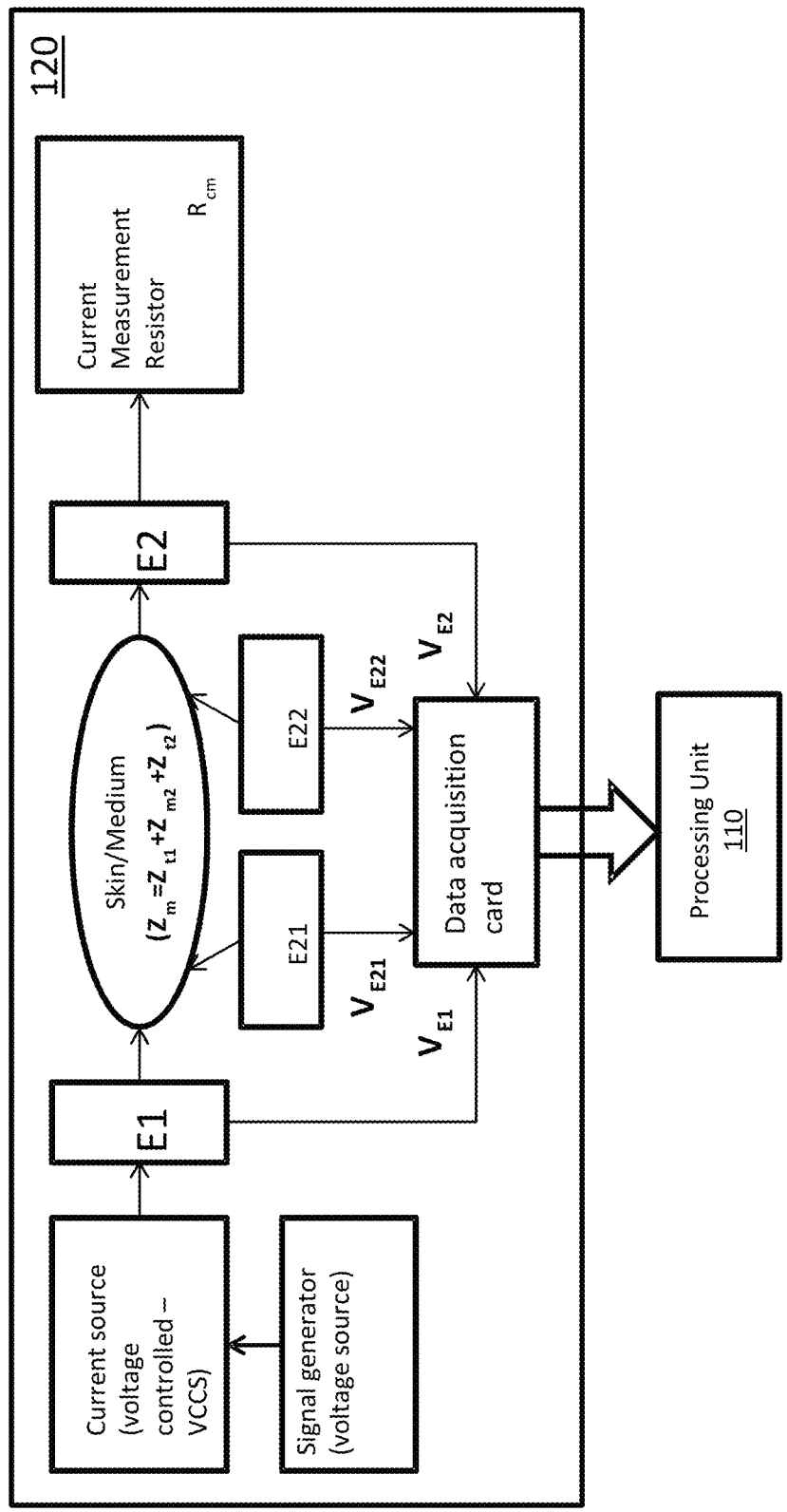
FIG. 5 illustrates a schematic diagram of the electrical impedance spectroscopy device comprising two pair of electrodes according to an embodiment of the present invention.
Figure 6:
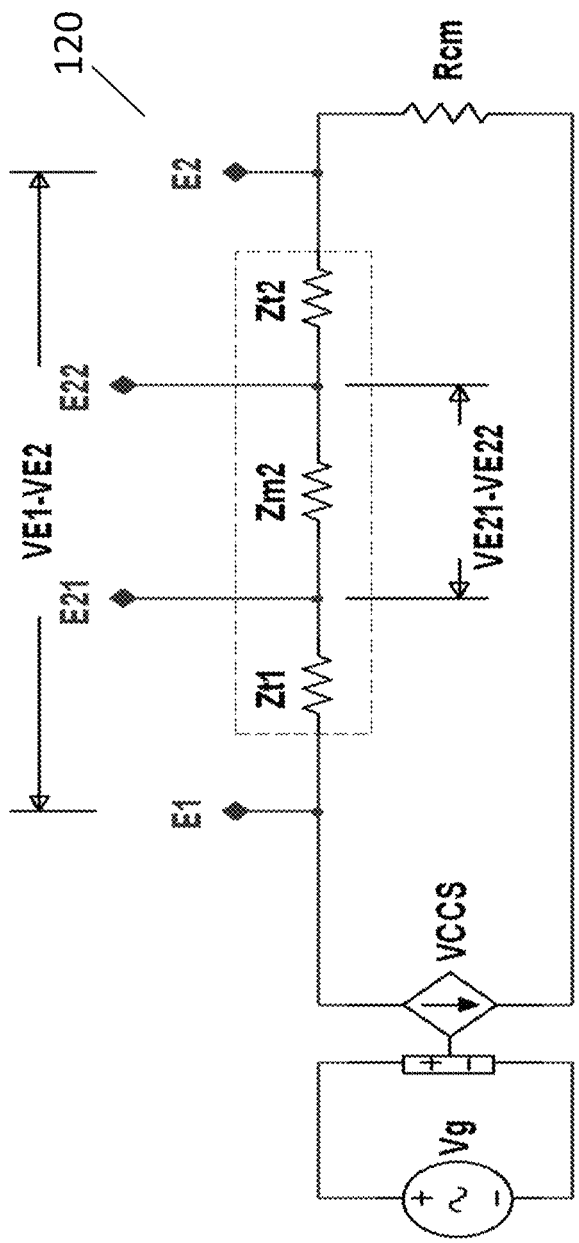
FIG. 6 illustrates an electrical schematic of the electrical impedance spectroscopy device shown in FIG. 5 according to an embodiment of the present invention.

Reference is now made to FIGS. 5 and 6 which provide schematic diagrams of an exemplary electrical impedance spectroscopy device 120. The device 120 shown in these figures is substantially similar to that described with reference to FIGS. 2 to 4, although, in this case the device 120 comprises two pair of electrodes. In particular, the device 120 comprises an additional second pair of electrodes E21 and E22 which is placed between the first pair of electrodes E1 and E2 as shown in the schematic diagram of FIG. 6.

In this exemplary device, the AC current signal of a desired frequency and amplitude is applied by the VCCS to the input electrode E1 and two differential voltages are obtained. The first differential voltage $V_m$ is obtained between the first pair of electrodes E1 and E2 as $V_m=V_{E1}-V_{E2}$ whereas the second differential voltage $V_2$ is obtained between the second pair of electrodes E21 and E22 as $V_2=V_{E21}-V_{E22}$. The measured impedance of the medium $Z_{m2}$ as measured by the electrodes E21 and E22, can be obtained as the ratio of the differential voltage between the electrodes E21-E22 and output current $I_{out}$:

$$Z_{m2} = \frac{V_{E21} - V_{E22}}{I_{out}} = \frac{V_2}{I_{out}} \qquad (10)$$

Accordingly, the total resistance $Z_m$ of the medium is the sum of the individual resistances:

$$Z_m = Z_{t1} + Z_{m2} + Z_{t2} \qquad (11)$$

where $Z_{t1}$ is the equivalent impedance of the medium between electrodes E1 and E21 and $Z_{t2}$ is the equivalent impedance of the medium between electrodes E2 and E22. The output current $I_{out}$ via $V_{CM}$, and output voltages $V_{E1}$, $V_{E21}$, $V_{E22}$ and $V_{E2}$ are recorded by the data acquisition card having high sampling rate (500 kS/s) and resolution (24 bit), providing two important advantages: a) measurement of electrical signals with maximum frequency in the order of several hundreds of kHz (typical frequency range 1-250 kHz) due to the high sampling rate and b) measurement of extremely low voltages in the order of microvolts due to high resolution of 24 bit. With the present invention, the measurement sensitivity is improved several orders of magnitude, providing capability for detection of small impedance fluctuations $$\frac{dZ_m}{Z_m} \text{ and } \frac{dZ_{m2}}{Z_{m2}}$$

in the order of μ0.01%. Thus, it is possible to detect extremely small variations of the measured impedance due to the flow of blood in the artery under assessment with unprecedented sensitivity.

Various modification will be apparent to those skilled in the art. For example, the device 120 may comprise more than two pair of electrodes attached to the skin of a limb of the person along a portion of the artery under assessment.

Figure 7:
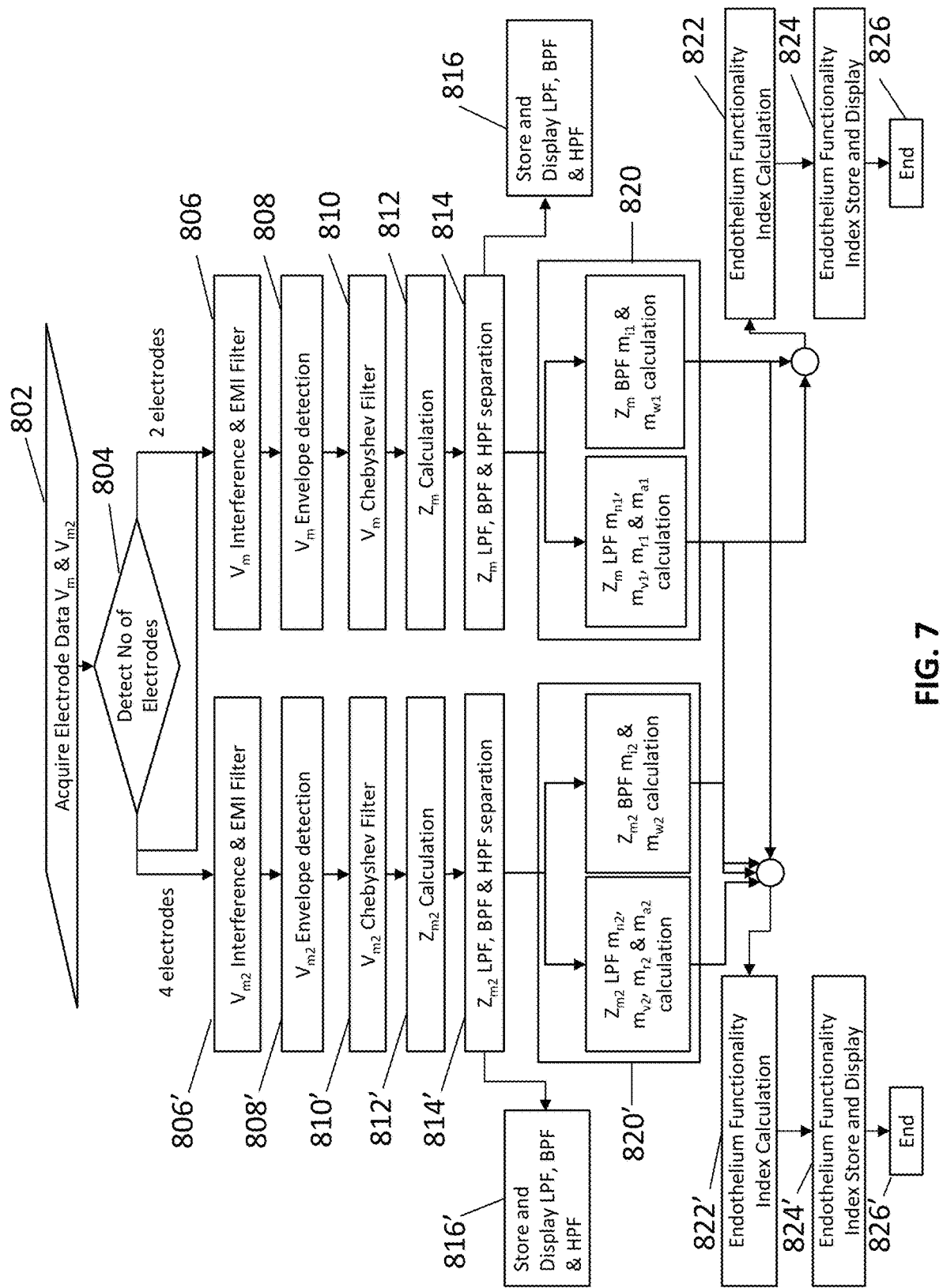
FIG. 7 illustrates a method for determining a vascular endothelium functionality of an artery of a person according to embodiments of the present invention, using up to two pairs of electrodes.

FIG. 7 is a flowchart showing an exemplified process 800 for determining the vascular endothelium functionality of an artery of a person. The process 800 can be implemented by the processing unit 110 communicatively coupled to the electrical impedance spectroscopy device 120. The processing unit 110 may further be in the form a remote server or equivalent.

The exemplified process 800 begins at 802, whereby the processing unit 110 acquires measurement data associated with a series of electrical measurements taken by an impedance spectroscopy device. In this case the data is voltage $V_m$ and/or $V_{m2}$.

Alternatively or in addition the process 800 may be configured to directly acquire at 802 impedance measurement data associated with a series of impedance measurements taken by an electrical impedance spectroscopy device. In this scenario, the voltage measurements $V_m$ and/or $V_{m2}$ are processed to obtain respective impedance of the medium $Z_m$ and/or $Z_{m2}$ before acquisition. The processing can be performed by an additional or existing processing unit of the system 100.

In the example process 800, the electrical measurements are associated with a series of voltage measurements taken by an electrical impedance spectroscopy device, such as the impedance spectroscopy device 120 shown in FIGS. 1-6 The electrical measurements are taken using at least one pair of electrodes attached to the skin of a limb of the person along a portion of an artery under assessment. These measurements are obtained over a period of time at different frequencies while the impedance spectroscopy device operates an ischemic cuff positioned on the limb of the person, such as the ischemic cuff 130 shown in FIG. 1. The ischemic cuff is operated between a normal state, ischemic state and a hyperaemic state as described with reference to FIGS. 1-7.

After acquiring measurement data, the process 800 proceeds at 804, whereby the number of electrode pairs of the impedance spectroscopy device is detected from the voltage measurement data. For example, the processing unit 110 can be configured to detect from the measurement data the time series corresponding to each electrode pair used by the impedance spectroscopy device to take the electrical measurements. If the number of electrode pairs of the impedance spectroscopy device is one (the impedance spectroscopy device has two electrodes, E1 and E2), the process proceeds at 806 whereby the voltage/impedance measurement data is filtered using a digital non-linear zero-phase filter to obtain filtered data. The filter may comprise an Infinite Impulse Response, IIR, Butterworth filter.

In the next steps the filtered data is digitally processed to obtain recovered data. In particular, at step 808 the process generates an envelope signal of the filtered data by calculating the absolute value of the filtered data. The absolute data is then digitally filtered at 810 through the software by means a low-pass digital filter such as a Chebyshev type I digital low-pass IIR filter with a standard cut-off frequency of about 100 Hz. At this point recovered data is obtained and the process 800 can continue by processing the recovered data to determine the impedance time series at step 812. The impedance time values can be obtained by applying the equation 2.

It is appreciated that if the process in 810 directly acquires impedance measurement data associated with a series of impedance measurements taken by the impedance spectroscopy device, the process does not require further processing the recovered data to determine the impedance time series using equations 2 or 10.

The example process 800 proceeds at 814 in which impedance time series are extracted from the measurement data associated with the electrical measurements for each pair of electrodes (in this case one pair). The process 800 further perform filtering of the impedance time series in the frequency domain. In this way the process extracts at least a low pass frequency, LPF, component waveform and a band limited frequency, BPF, component waveform for each pair of electrodes. The LPF component includes the calculated mean impedance (0 Hz frequency) of the impedance time series. The BPF is known as cardiac component of the impedance time series. The LPF is a slow varying component with respect to cardiac component, because the period of the shortest LPF signal is at least two times longer than the longest period of BPF signal. In addition, at 814 the processor 800 may further perform filtering of the impedance time series in the frequency domain to extracts a high frequency, HPF, component waveform. This component comprises high frequency waveform of the impedance time series having frequency greater than 10 Hz. The HPF component comprises harmonics of the cardiac component and measurement noise.

The filtering of the impedance time series in the frequency domain may include applying a set of filters having the following characteristics:

1) For the LPF component the filter may be a low pass filter IIR Butterworth of 4th order with a cut-off frequency of −3 dB at 0.5 Hz.
2) For the BPF component the filter may be a band pass filter of 4th order IIR Butterworth with a lower cut-off frequency of −3 dB at 0.5 Hz and upper cut-off frequency at 10 Hz.
3) For the HPF component the filter may be a 4th order IIR Butterworth high-pass filter with a cut-off frequency of −3 dB at 10 Hz.

After filtering, the process 800 proceeds at step 816 in which the components are stored in a memory of the system 100. In addition or alternative, the isolated components may be displayed by means of a display module 140 or may be transmitted to another terminal, such as a remote device or server 300.

In the next steps, the process determines the vascular endothelium functionality of the artery of the person using the LPF and BPF component waveforms obtained from the pair of electrodes E1 and E2. In particular, the process 800 proceeds at step 820 whereby the LPF and BPF component waveforms are processed to extract a set of biomarker parameter values. Each biomarker parameter is indicative of a particular aspect of the endothelium functionality of the artery of the person.

Figure 8:
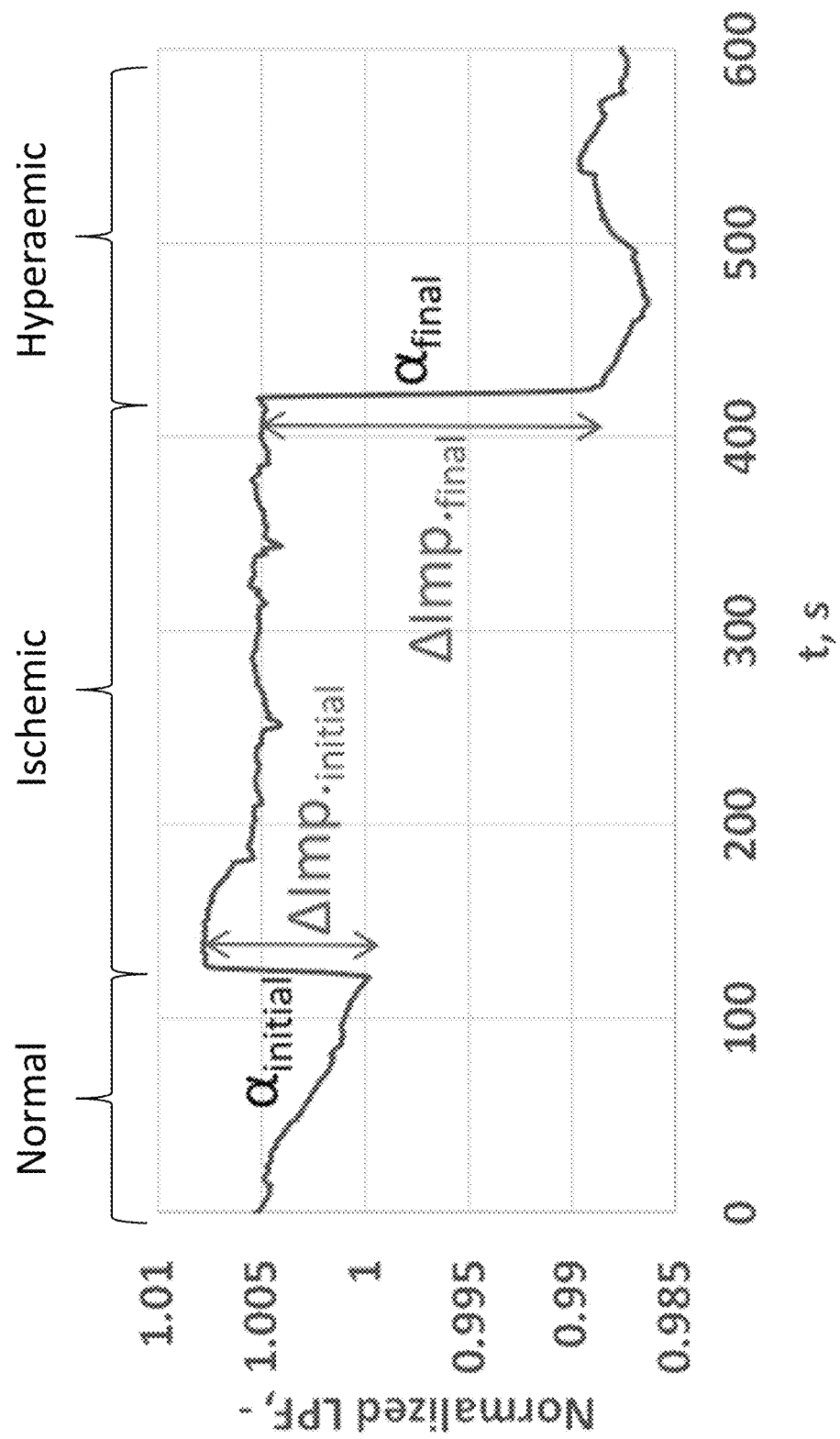
FIG. 8 shows an exemplified LPF waveform extracted from measurement data obtained during the operation of the ischemic cuff by an electrical impedance spectroscopy device according to embodiments of the present invention.

Reference is now made to FIGS. 8 to 12 which show LPF component waveforms obtained from each pair of electrodes. These figures show how the LPF component waveform transitions between the normal state, the ischemic state and the hyperaemic state, as shown in FIG. 8.

By processing the LPF component waveform, a set of biomarker parameter values are obtained.

The set of biomarker parameter values may comprise biometric parameter value $m_n$, which is determined as the change in an impedance value of the LPF component waveform measured during a transition of the ischemic cuff from the normal state to the ischemic state:

$$m_n = \Delta Imp_{initial} \qquad (12)$$

wherein $\Delta Imp_{initial}$ is a change in impedance of the LPF component waveform associated with a transition from the normal to the ischemic state.

The biomarker parameter value $m_n$, has been studied by means of clinical trials which gathered preliminary clinical data from a poll of persons affected by coronary heart disease and healthy persons. The clinical data has been evaluated using the sensitivity and specificity of the clinical parameters. The sensitivity of a clinical data refers to the ability of the clinical test to correctly identify persons with coronary heart disease. Clinical trials have shown a sensitivity parameter of about 82% for people suffering of coronary heart disease and, in this case, the $m_n$ value was lower than 0.8. In contrast, the specificity of a clinical data refers to the ability of the test to correctly identify persons without the disease. Clinical trials have shown a specificity parameter of about 80% for healthy people and, in this case, the $m_n$ value was greater than 1.5, which indicates healthy endothelium functionality.

The set of biomarker parameter values may further comprise the determination of biometric parameter value my which is determined as the ratio between: (i) a change in an impedance value of the LPF component waveform measured during a transition of the ischemic cuff from the normal state to the ischemic state, and (ii) a change in an impedance value of the LPF component waveform measured during a transition of the ischemic cuff from the ischemic state to the hyperaemic state. Accordingly, the my parameter can be defined as:

$$m_y = \left| \frac{\Delta Imp_{initial}}{\Delta Imp_{final}} \right| \quad (13)$$

wherein:

$\Delta Imp_{initial}$ is a change in impedance of the LPF component waveform associated with the transition from the normal to the ischemic state; and $\Delta Imp_{final}$ is a change in impedance of the LPF component waveform associated with a transition from the ischemic to the hyperaemic state.

Figure 9A:
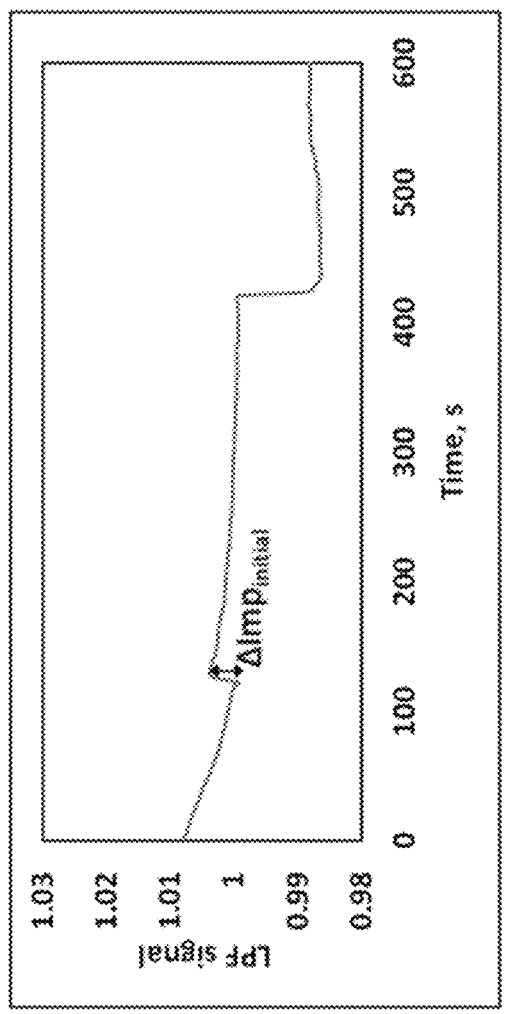
FIGS. 9 to 12 show exemplified LPF component waveforms and the relevant key parameters for the calculation of the biometrics, obtained using the method of FIG. 7 from people showing signs of cardiovascular disease (a) and corresponding waveforms from people considered to be healthy (b) according to embodiments of the present invention.
Figure 9B:
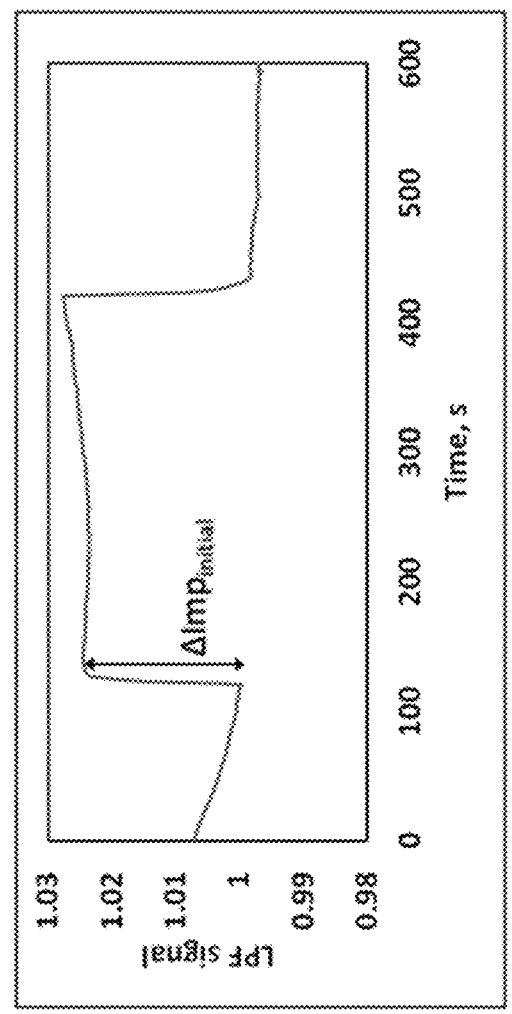
Figure 10A:
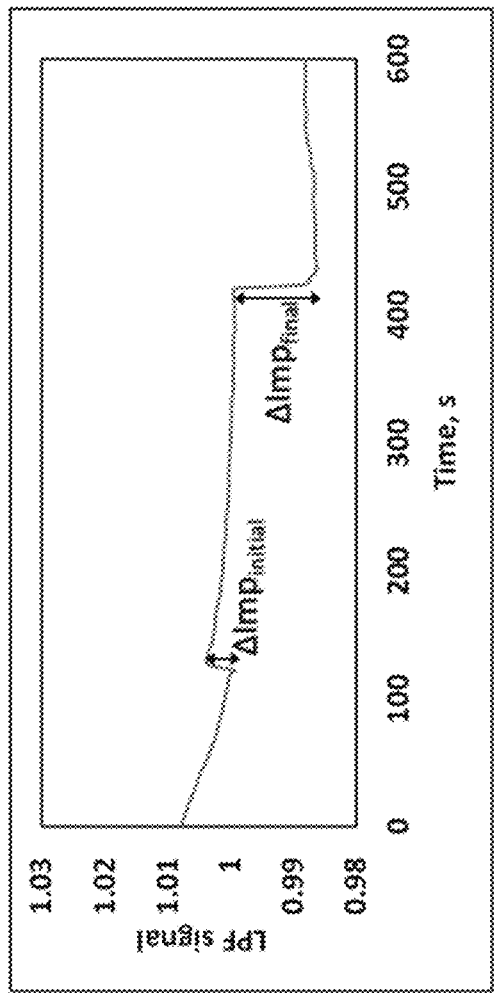
Figure 10B:
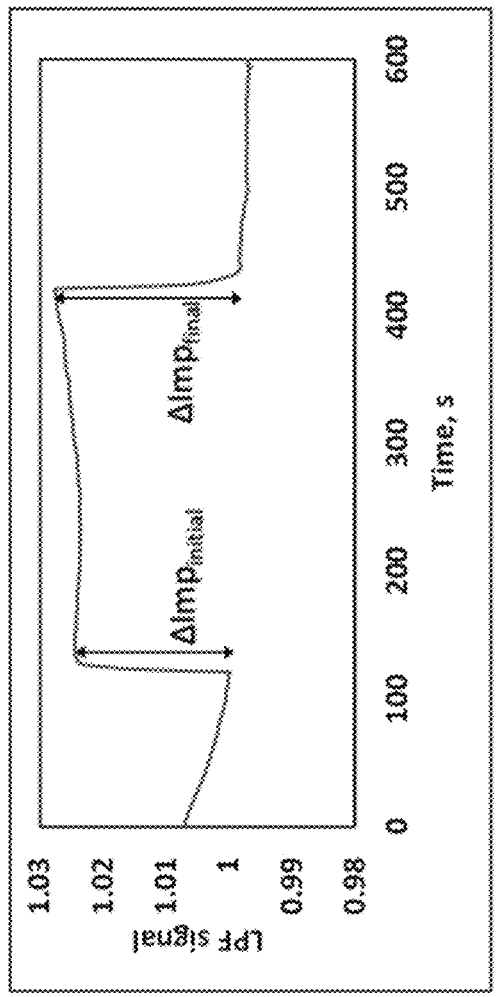

With reference to this biomarker parameter value, clinical trials have shown a sensitivity parameter of about 75% for people suffering of coronary heart disease as shown in FIG. 10a and, in this case, the my value was lower than 0.4. In contrast, the specificity parameter was about 88% for healthy people and the my value was greater than 0.6, as shown in FIG. 10b, which indicates healthy endothelium functionality. FIG. 9a and FIG. 9b show an example of the LPF response associated with people suffering from a cardiovascular disease and healthy people respectively.

The set of biomarker parameter values may further comprise the determination of biometric parameter value $m_r$, which is determined as a gradient of an impedance value of the LPF component waveform measured during a transition of the ischemic cuff from the normal state to the ischemic state:

$$m_r = \alpha_{initial} \quad (14)$$

wherein:

$\alpha_{initial}$ is the gradient of the impedance of the LPF component waveform associated with the transition from the normal to the ischemic state.

Figure 11A:
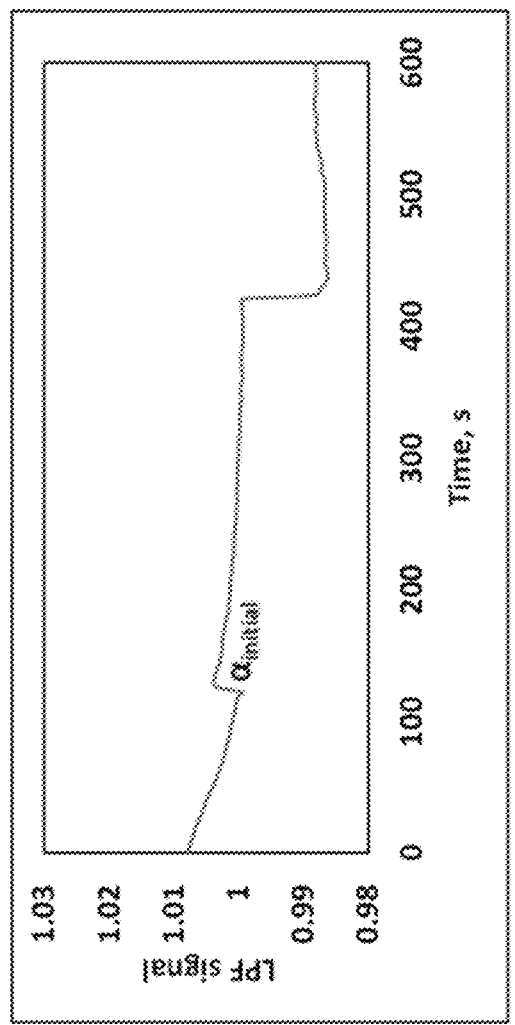
Figure 11B:
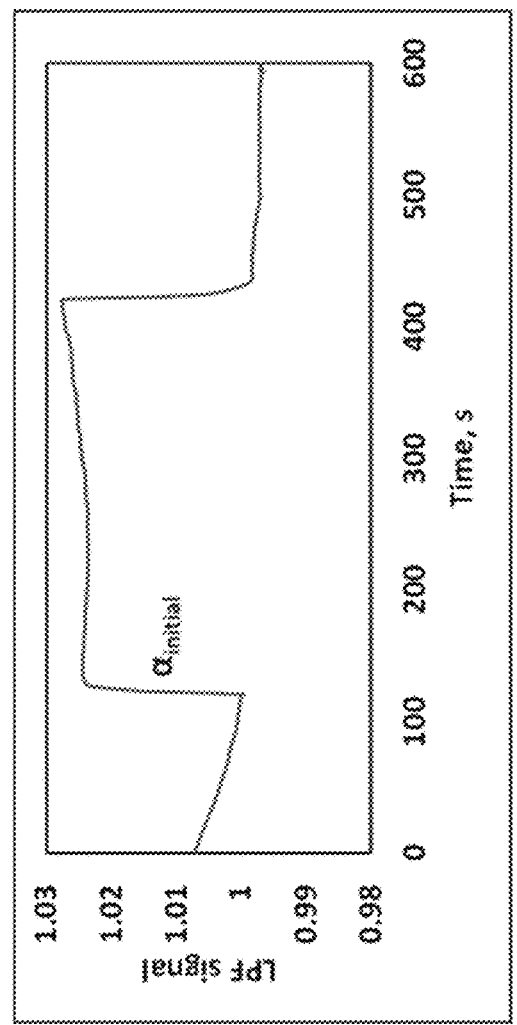

With reference to biomarker parameter value $m_r$, clinical trials have shown a sensitivity parameter of about 93% for people suffering of coronary heart disease, and, in this case, the $m_r$ value was lower than 0.002, as shown in FIG. 11a. In contrast, the specificity parameter was about 82% for healthy people and the $m_r$ value was greater than 0.006, which indicates healthy endothelium functionality, as shown in FIG. 11b.

The set of biomarker parameter values may further comprise the determination of biometric parameter value $m_\alpha$, which is determined as a ratio between: (i) a gradient of an impedance value of the LPF component waveform measured during a transition of the ischemic cuff from the normal state to the ischemic state, and (ii) a gradient of an impedance value of the LPF component waveform measured during a transition of the ischemic cuff from the ischemic state to the hyperaemic state. Accordingly, the $m_\alpha$ parameter can be defined as:

$$m_a = \left| \frac{\alpha_{initial}}{\alpha_{final}} \right| \quad (15)$$

wherein:

$\alpha_{initial}$ is the gradient of the impedance of the LPF component waveform associated with the transition from the normal to the ischemic state; and $\alpha_{final}$ is the gradient of the impedance of the LPF component waveform associated with the transition from the ischemic state to the hyperaemic state.

Figure 12A:
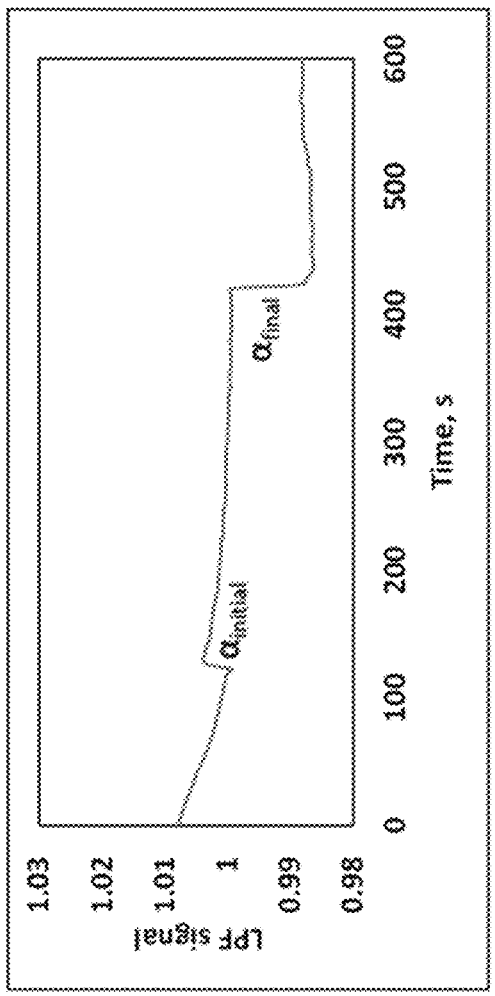
Figure 12B:
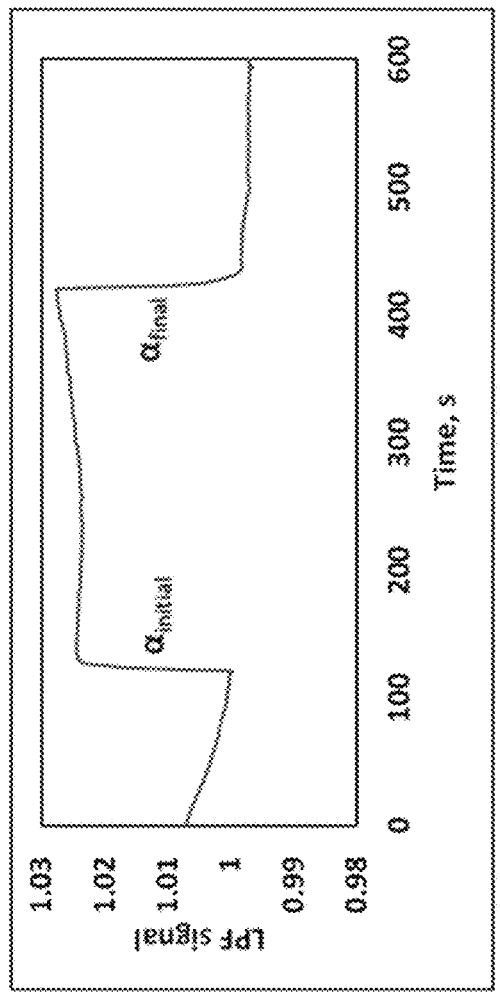

With reference to biomarker parameter value $m_a$, clinical trials have shown a sensitivity parameter of about 89% for people suffering of coronary heart disease and, in this case, the $m_a$ value was lower than 0.5, as shown in FIG. 12a. In contrast, the specificity parameter was about 82% for healthy people and the $m_\alpha$ value was greater than 0.8, which indicates healthy endothelium functionality, a shown in FIG. 12b.

Figure 13:
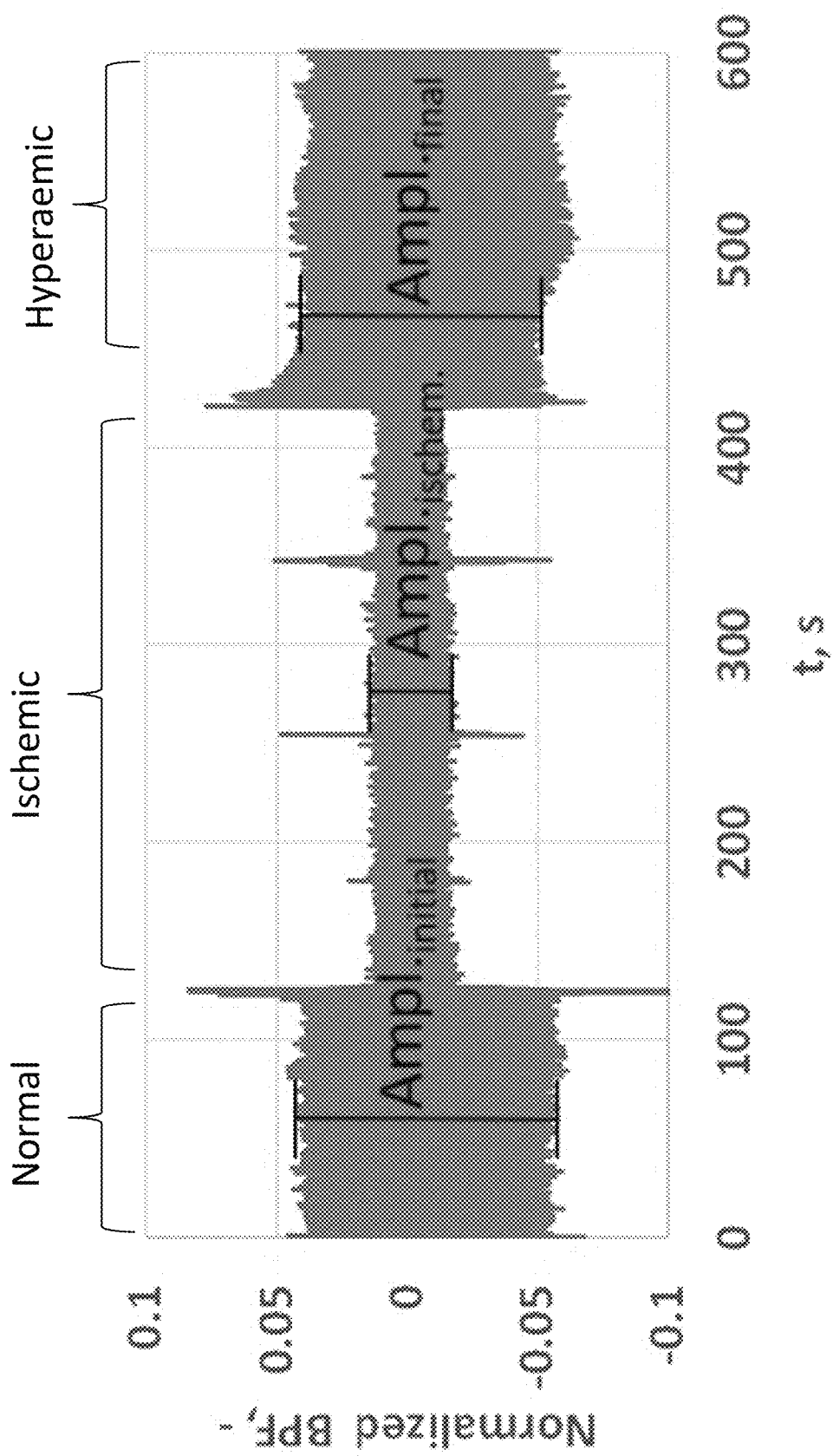
FIG. 13 shows an exemplified BPF waveform component extracted from measurement data obtained during the operation of the ischemic cuff by an electrical impedance spectroscopy device according to embodiments of the present invention.

Reference is now made to FIGS. 13 to 15 showing BPF component waveforms obtained from the electrodes. These figures show the amplitude of the waveform during the normal state the ischemic state and the hyperaemic state, as shown in FIG. 13. Further biometric parameter values are extracted from the BPF component waveform, which are combined with the biometric parameters obtained from the LPF component waveform, as described previously.

Figure 14A:
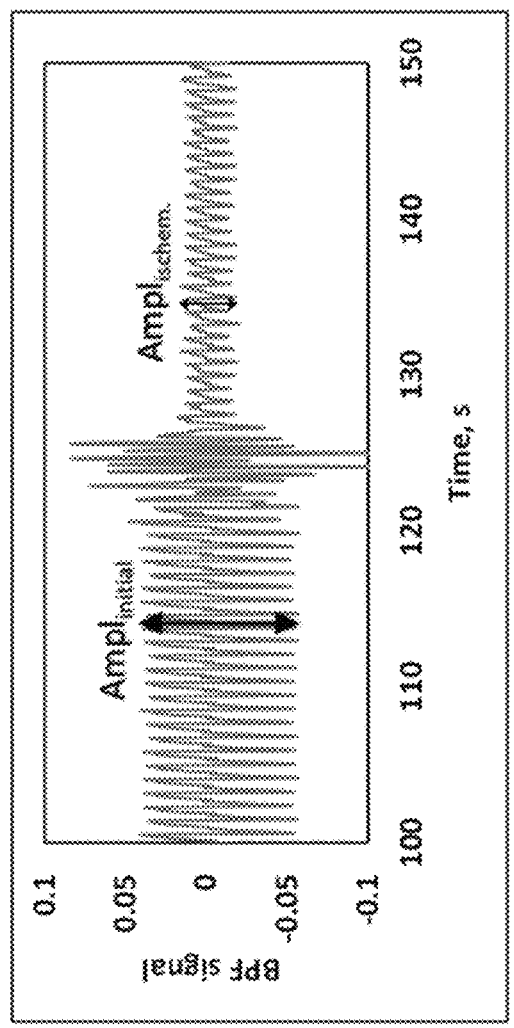
FIGS. 14 and 15 show exemplified BPF component waveforms and the relevant key parameters for the calculation of the biometrics, obtained using the method of FIG. 7 from people showing signs of cardiovascular disease (a) and corresponding waveforms from people considered to be healthy (b) according to embodiments of the present invention.
Figure 14B:
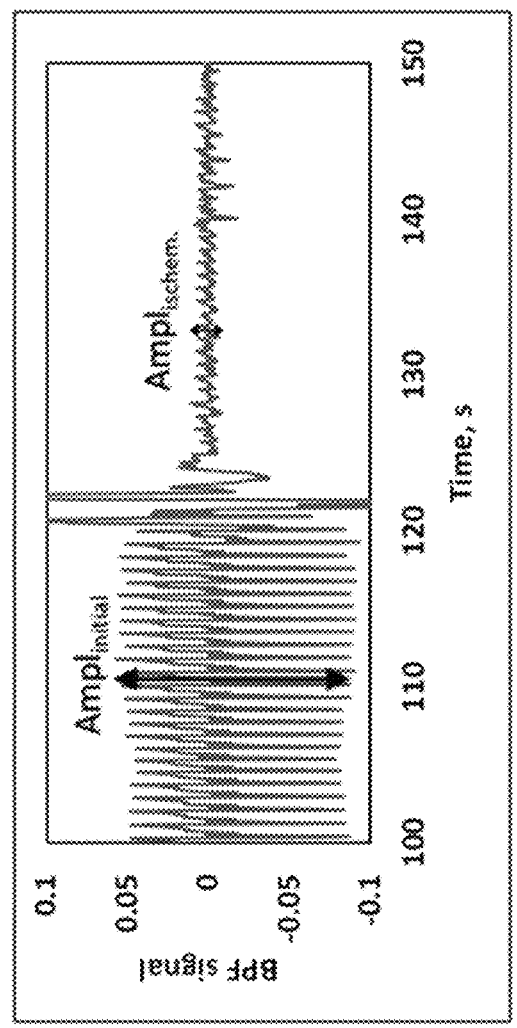

The set of biomarker parameter values extracted from the BPF component waveform may comprise biometric parameter value $m_i$ which is determined as a ratio between: (i) an amplitude value of the BPF component waveform measured during the operation of the ischemic cuff in the ischemic state; and (ii) an amplitude value of the BPF component waveform measured during the operation of the ischemic cuff in the normal state. Accordingly, the $m_i$ parameter may be defined as:

$$m_i = \frac{Ampl_{ischem.}}{Ampl_{initial}} \quad (17)$$

wherein:

$Ampl_{ischem.}$ is an amplitude of the BPF component waveform associated with the ischemic state, as shown in FIGS. 14a and 14b; and $Ampl_{initial.}$ is an amplitude of the BPF component waveform associated with the normal state, as shown in FIGS. 14a and 14b.

With reference to biomarker parameter value $m_i$, clinical trials have shown a sensitivity parameter of about 75% for people suffering of coronary heart disease and, in this case, the $m_i$ value was greater than 0.3. In contrast, the specificity parameter was about 72% for healthy people and the $m_i$ value was lower than 0.2, which indicates healthy endothelium functionality.

Figure 15A:
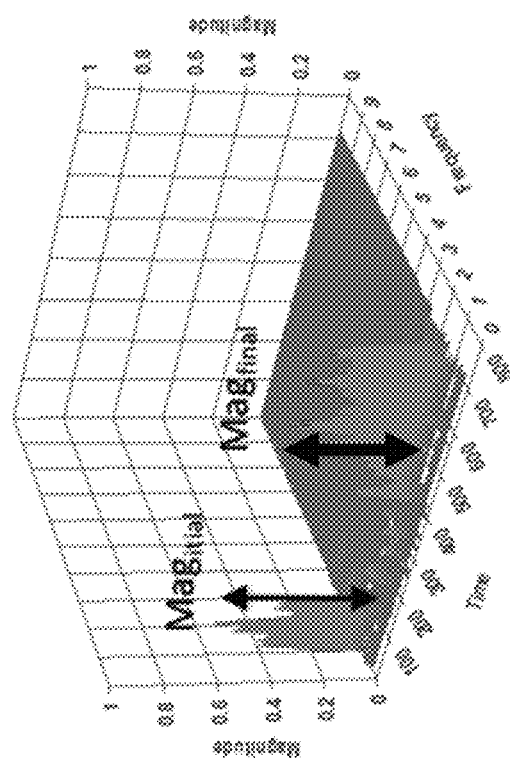
Figure 15B:
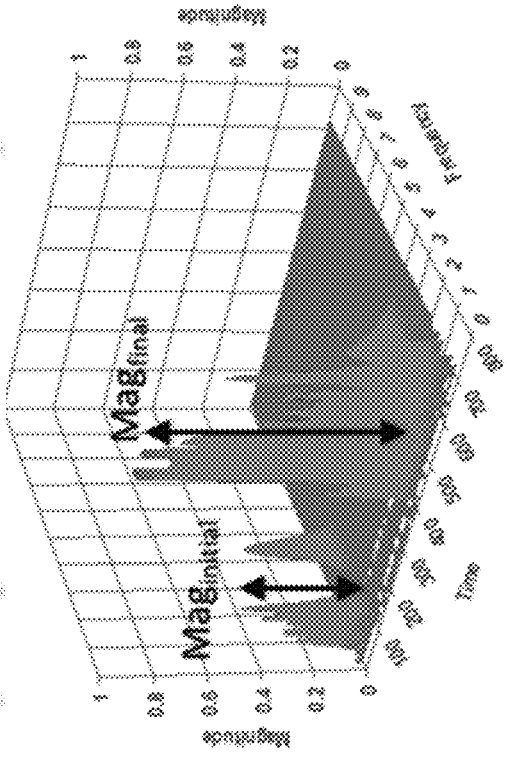

Reference is now made to FIGS. 15a and 15b which shows BPF component waveform as a function of frequency and time after applying a Continuous Wavelet Transform, CWT, with Morlet basis function, for people suffering from cardiovascular diseases (CAD) and healthy people respectively.

From the BPF component waveform shown in FIGS. 15a and 15b biometric parameter value $m_w$ is determined as a ratio between: (i) an amplitude value of the CWT of the BPF component waveform extracted from measurement data obtained during the operation of the ischemic cuff in the hyperaemic state, and (ii) an amplitude value of a CWT of the BPF component waveform extracted from measurement data obtained during the operation of the ischemic cuff in the normal state. Accordingly, the $m_w$ parameter may be defined as:

$$m_w = \frac{Mag_{final}}{Mag_{initial}} \quad (18)$$

wherein:
$Mag_{final}$ is a width of the CWT of the BPF component waveform associated with the hyperaemic state; and
$Mag_{initial}$ is a with of a CWT of the BPF component waveform associated with the normal state.

With reference to biomarker parameter value $m_w$, clinical trials have shown a sensitivity parameter of about 78% for people suffering of coronary heart disease and, in this case, the $m_w$ value was lower than 1, a shown in FIG. 15a. In contrast, the specificity parameter was about 74% for healthy people and the $m_w$ value was greater than 1.2 indicating healthy endothelium functionality, as shown in FIG. 15b.

It will be appreciated that the set of biomarker parameter values can include one or more of the biomarker values $m_a$, $m_i$, $m_w$, $m_n$, $m_v$ and $m_r$ described above.

Reference is now made again to the process 800 in FIG. 7. In response to extracting the set of biomarker parameter values from the LPF and BPF component waveforms, the process 800 proceeds at step 822 in which it is determined, based on the biomarker parameter values, an endothelium functionality index indicative of the vascular endothelium functionality of the artery of the person. For example, the index may be extracted based on all or a selection of biomarker parameter values extracted from the LPF and BPF component waveforms, as mentioned above. For example, for the determination of coronary disease the six biomarker parameters $m_a$, $m_i$, $m_w$, $m_n$, $m_v$ and $m_r$, may be used to determine the endothelium functionality index as follows:

$$index = \frac{(10^2 \cdot m_n) + m_v + (1.25 \cdot m_r \cdot 10^2) + (1.25 \cdot m_a) + (0.75 \cdot m_w)}{(0.75 \cdot m_i)} \quad (19)$$

It is appreciated however that further biometric parameter values may be extracted and used for the determination of the endothelium functionality index.

For example, the BPF component waveform showing in FIGS. 14a and 14b may be processed to further extract biomarker parameter $m_r$ which is determined as the ratio between: (i) an amplitude value of the BPF component waveform measured during the operation of the ischemic cuff in the ischemic state, and (ii) an amplitude value of the BPF component waveform measured during the operation of the ischemic cuff in the hyperaemic state. Accordingly, the $m_r$ parameter may be defined as:

$$m_f = \frac{Ampl_{ischem.}}{Ampl_{final}} \quad (16)$$

wherein:
$Ampl_{ischem.}$ is an amplitude of the BPF component waveform associated with the ischemic state; and
$Ampl_{final}$ is an amplitude of the BPF component waveform associated with the hyperaemic state.

With reference to biomarker parameter value $m_r$, clinical trials have shown a sensitivity parameter of about 75% for people suffering of coronary heart disease and, in this case, the $m_r$ value was greater than 0.3, as shown in FIG. 14a. In contrast, the specificity parameter was about 72% for healthy people and the $m_r$ value was lower than 0.2, which indicates healthy endothelium functionality as shown in 14b.

The endothelium functionality index may then be compared to a reference index. With reference to endothelium functionality index, clinical trials have shown a sensitivity parameter of about 92% for people suffering of coronary heart disease and, in this case, the endothelium functionality index was lower than 15. In contrast, the specificity parameter was about 97% for healthy people and the endothelium functionality index value was greater than 25 indicating healthy endothelium functionality.

The process 800 proceeds at step 824 in which the endothelium functionality index is stored in a memory of the system 100. In addition or alternative, the endothelium functionality index may be displayed by means of a display module 140 and/or may be transmitted to another terminal, such as a remote server 300 or user device.

At this point, the process 800 proceeds at 826 and ends, or it is repeated as needed. The assessment of the endothelial function is a critical tool in the hands of clinical practitioners or users. Based on the endothelium functionality index obtained by the present invention, it is possible to assess with high accuracy the condition of the endothelium functionality of an artery and accordingly determine whether the person under assessment is at risk of a cardiovascular disease and recommend a treatment or therapy to follow.

The impedance spectroscopy device 120 may comprises two or more pair of electrodes as shown in FIGS. 5 and 6. As such, the process 800 after detecting at 804 the number of electrode pairs of the impedance spectroscopy device, the process performs the steps 806' to 826' in addition to the steps 806 to 826 described above for each pair of electrodes.

The steps 806' to 826' are substantially similar to the steps 806 to 826. These additional steps are directed to the second pair of electrodes E21 and E22 which is placed between the first pair of electrodes E1 and E2. In this case the impedance time series can be obtained by applying the equation 2 for the first pair of electrodes at 812 and equation 10 for the second pair of electrodes at 812'. In this scenario each of the biomarker parameter values is obtained by performing a weighted arithmetic mean of corresponding biomarker parameter values obtained from each detected pair of electrodes. In the case of two pairs of electrodes, each biometric parameter in the set may be obtained as follows. In particular:

The biomarker parameter $m_n$ can be obtained as:

$$m_n = \frac{1}{3}m_{n1} + \frac{2}{3}m_{n2} \qquad (20)$$

wherein $m_{n1}$ is the biomarker parameter value obtained for the first pair of electrodes E1 and E2 and $m_{n2}$ is the biomarker parameter value obtained for the second pair of electrodes E21 and E22.

With reference to the biomarker parameter value $m_n$, clinical trials have estimated that for healthy persons $m_n$ is greater than 1.5 while for person suffering of coronary heart disease $m_n$ is lower than 0.8.

The biomarker parameter my can be obtained as:

$$m_v = \frac{1}{3}m_{v1} + \frac{2}{3}m_{v2} \qquad (21)$$

wherein $m_{v1}$ is the biomarker parameter value obtained for the first pair of electrodes E1 and E2 and $m_{v2}$ is the biomarker parameter value obtained for the second pair of electrodes E21 and E22.

With reference to the biomarker parameter value my, clinical trials have estimated that for healthy persons my is greater than 0.6 while for person suffering of coronary heart disease my is lower than 0.4.

The biomarker parameter $m_r$ can be obtained as:

$$m_r = \frac{1}{2}m_{r1} + \frac{1}{2}m_{r2} \qquad (22)$$

wherein $m_{r1}$ is the biomarker parameter value obtained for the first pair of electrodes E1 and E2 and $m_{r2}$ is the biomarker parameter value obtained for the second pair of electrodes E21 and E22.

With reference to the biomarker parameter value $m_r$, clinical trials have estimated that for healthy persons $m_r$ is greater than 0.006 while for person suffering of coronary heart disease $m_r$ is lower than 0.002.

The biomarker parameter $m_a$ can be obtained as:

$$m_a = \frac{1}{2}m_{a1} + \frac{1}{2}m_{a2} \qquad (23)$$

wherein $m_{\alpha 1}$ is the biomarker parameter value obtained for the first pair of electrodes E1 and E2 and $m_{\alpha 2}$ is the biomarker parameter value obtained for the second pair of electrodes E21 and E22.

With reference to the biomarker parameter value $m_\alpha$, clinical trials have estimated that for a healthy person $m_\alpha$ is greater than 0.8 while for person suffering of coronary heart disease $m_y$ is lower than 0.5.

The biomarker parameter $m_i$ can be obtained as:

$$m_i = 0.45\, m_{i1} + 0.55\, m_{i2} \qquad (24)$$

wherein $m_{i1}$ is the biomarker parameter value obtained for the first pair of electrodes E1 and E2 and $m_{i2}$ is the biomarker parameter value obtained for the second pair of electrodes E21 and E22.

With reference to the biomarker parameter value $m_i$, clinical trials have estimated that for a healthy person mi is lower than 0.2 while for person suffering of coronary heart disease mi is greater than 0.3.

The biomarker parameter $m_f$ can be obtained as:

$$m_f = 0.45\, m_{f1} + 0.55\, m_{f2} \qquad (25)$$

wherein $m_{f1}$ is the biomarker parameter value obtained for the first pair of electrodes E1 and E2 and $m_{f2}$ is the biomarker parameter value obtained for the second pair of electrodes E21 and E22.

With reference to the biomarker parameter value $m_f$, clinical trials have estimated that for a healthy person $m_f$ is lower than 0.2 while for person suffering of coronary heart disease $m_f$ is greater than 0.3.

The biomarker parameter $m_w$ can be obtained as:

$$m_w = 0.40\, m_{w1} + 0.60\, m_{w2} \qquad (26)$$

wherein $m_{w1}$ is the biomarker parameter value obtained for the first pair of electrodes E1 and E2 and $m_{w2}$ is the biomarker parameter value obtained for the second pair of electrodes E21 and E22.

With reference to the biomarker parameter value $m_w$, clinical trials have estimated that for a healthy person mw is greater than 1.2 while for person suffering of coronary heart disease mw is lower than 1.

Various modification will be apparent to those skilled in the art. For example, in the event that the device 120 comprises more than two pairs of electrodes, the process will proceed to extract impedance time series from the measurement data associated with electrical measurements acquired from each additional pair of electrodes. The process will thus substantially repeat steps 806' to 826' for each additional pair of electrodes.

In this scenario each of the biomarker parameter values is obtained by performing a weighted arithmetic mean of corresponding biomarker parameter values obtained from each detected pair of electrodes. The weighs may be based to the respective position of the electrode pairs placed along the artery of the person.

The invention claimed is:

1. A computer implemented method for determining a vascular endothelium functionality of an artery of a person, the method comprising steps of:
    acquiring measurement data associated with a series of electrical measurements obtained by an electrical impedance spectroscopy device using at least one pair of electrodes attached to a skin portion of a limb of the person along a portion of the artery under assessment, the electrical measurements being obtained over a period of time at different frequencies while the impedance spectroscopy device operates an ischemic cuff positioned on the limb of the person between a normal state, where no pressure is applied on the limb of the person, an ischemic state, where a desired pressure is applied on the limb of the person to restrict flow of blood in the artery under assessment, and a hyperaemic state, where the pressure applied during the ischemic state is released;
    extracting, from the measurement data, an impedance time series associated with impedance changes of a medium intervening between the at least one pair of electrodes, the medium comprising the portion of the artery, surrounding tissue, the skin portion, and the flow of blood in the artery during the normal state, ischemic state, and hyperaemic state;

filtering the impedance time series in a frequency domain to extract at least a low pass frequency (LPF) component waveform and a band limited frequency (BPF) component waveform for each of the at least one pair of electrodes; and determining the vascular endothelium functionality of the artery of the person by performing the steps of:

processing the LPF and BPF component waveforms obtained from each of the at least one pair of electrodes to extract a set of biomarker parameter values, each biomarker parameter being indicative of an aspect of the endothelium functionality of the artery of the person; and determining, based on the biomarker parameter values, an endothelium functionality index indicative of the vascular endothelium functionality of the artery of the person; and characterised in that the step of extracting a set of biomarker parameter values comprises the step of determining a biomarker parameter value ma as a ratio between:

a gradient of an impedance value of the LPF component waveform measured during a transition of the ischemic cuff from the normal state to the ischemic state, and a gradient of an impedance value of the LPF component waveform measured during a transition of the ischemic cuff from the ischemic state to the hyperaemic state.

2. The method of claim 1, wherein a step of determining the vascular endothelium functionality further comprises the step of comparing the endothelium functionality index with a reference index.

3. The method of claim 1, wherein extracting the set of biomarker parameter values comprises the step of:

detecting from the measurement data the impedance time series corresponding to each of the at least one electrode pair used by the impedance spectroscopy device to take the series of electrical measurements; and wherein if more than one pair of electrodes is detected performing the step of:

determining the value of each biometric parameter in the set by averaging the corresponding biometric parameter values obtained from the LPF and BPF component waveforms extracted from each of the detected at least one pair of electrodes.

4. The method of claim 1, wherein the step of extracting the set of biomarker parameter values comprises a step of determining a biomarker parameter value $m_n$ as a change in an impedance value of the LPF component waveform measured during a transition of the ischemic cuff from the normal state to the ischemic state.

5. The method of claim 1, wherein the step of extracting the set of biomarker parameter values comprises a step of determining a biomarker parameter value $m_v$ as a ratio between:

a change in an impedance value of the LPF component waveform measured during a transition of the ischemic cuff from the normal state to the ischemic state, and a change in an impedance value of the LPF component waveform measured during a transition of the ischemic cuff from the ischemic state to the hyperaemic state.

6. The method of claim 1, wherein the step of extracting the set of biomarker parameter values comprises a step of determining a biomarker parameter value $m_r$ as a gradient of an impedance value of the LPF component waveform measured during a transition of the ischemic cuff from the normal state to the ischemic state.

7. The method of claim 1, wherein the step of extracting the set of biomarker parameter values comprises a step of determining a biomarker parameter value $m_i$ as a ratio between:

an amplitude value of the BPF component waveform measured during operation of the ischemic cuff in the ischemic state; and an amplitude value of the BPF component waveform measured during operation of the ischemic cuff in the normal state.

8. The method of claim 1, wherein the step of extracting the set of biomarker parameter values comprises a step of determining a biomarker parameter value $m_w$ as a ratio between:

an amplitude value of a Continuous Wavelet Transform, CWT, of the BPF component waveform extracted from the measurement data obtained during operation of the ischemic cuff in the hyperaemic state, and an amplitude value of a CWT of the BPF component waveform extracted from measurement data obtained during operation of the ischemic cuff in the normal state.

9. The method of claim 4, wherein the step of determining an endothelium functionality index comprises determining the endothelium functionality index as:

$$\text{index} = \frac{\left[(10^2 \cdot m)_n\right] + m_v + \left[(1.25 \cdot m)_r \cdot 10^2\right] + \left[(1.25 \cdot m)_a\right] + (0.75 \cdot m_w)}{[(0.75 \cdot m)_i]}.$$

10. The method of claim 1, wherein the step of extracting the impedance time series comprises a step of:

filtering the measurement data using a digital zero-phase filter to obtain filtered data comprising an Infinite Impulse Response (IIR) Butterworth filter.

11. The method of claim 10, wherein the step of extracting the impedance time series further comprises:

digitally processing the filtered data to obtain recovered data by performing the steps of:

generating an envelope signal of the filtered data by calculating absolute data of the filtered data;

digitally filtering the envelope signal using a digital low-pass filter with a standard cut-off frequency of 100 Hz to obtain the recovered data, wherein the digital low-pass filter is Chebyshev Type I IIR filter; and processing the recovered data to determine the impedance time series.

12. A system for determining vascular endothelium functionality of an artery of a person comprising:

an ischemic cuff configured to be positioned on a limb of the person;

an electrical impedance spectroscopy device configured to obtain a series of electrical measurements over a period of time at different frequencies associated with the endothelium functionality of the artery under assessment, the impedance spectroscopy device comprising at least one pair of electrodes configured to be attached to a skin portion of the limb of the person along a portion of the artery under assessment to obtain the series of electrical measurements of a medium intervening between the at least one pair of electrodes, the medium comprising the portion of the artery, surrounding tissue, the skin portion, and blood flowing in the artery during the normal state, ischemic state, and hyperaemic state, wherein the impedance spectroscopy device is configured to operate, during obtaining the series of electrical measurements from the at least one pair of electrodes, the ischemic cuff between the normal state, where no pressure is applied on the limb of the person, the ischemic state, where a pressure is applied on the limb of the person to restrict flow of blood in the artery under assessment, and the hyperaemic state, where the pressure applied during the ischemic state is released;

a processing unit communicatively coupled to the impedance spectroscopy device and configured to perform the method of claim 1; and a display configured to display an endothelium functionality index determined by the processing unit, which is indicative of the vascular endothelium functionality of the artery of the person, and/or to display the results of a comparison between the determined endothelium functionality index and a reference endothelium functionality index.

13. The system of claim 12, wherein the impedance spectroscopy device comprises a first pair of electrodes and a second pair of the electrodes, wherein the second pair of electrodes is placed between the first pair of electrodes.

14. A computer program product comprising instructions which, when the program is executed by a computer, causes the computer to perform the method of claim 1.

* * * * *